(12) United States Patent
Tung

(10) Patent No.: US 6,500,623 B1
(45) Date of Patent: Dec. 31, 2002

(54) REPLICATION DEFECTIVE HIV VACCINE

(75) Inventor: Frank Yao Tsung Tung, Lawrenceville, GA (US)

(73) Assignee: Genecure LLP, Atlanta, GA (US)

( * ) Notice: Subject to any disclaimer, the term of this patent is extended or adjusted under 35 U.S.C. 154(b) by 0 days.

(21) Appl. No.: 09/700,304

(22) PCT Filed: May 12, 1999

(86) PCT No.: PCT/US99/10523

§ 371 (c)(1),
(2), (4) Date: Nov. 9, 2000

(87) PCT Pub. No.: WO99/58726

PCT Pub. Date: Nov. 18, 1999

Related U.S. Application Data

(60) Provisional application No. 60/085,115, filed on May 12, 1998.

(51) Int. Cl.[7] .......................... G01N 33/53; C12Q 1/70; C12Q 1/68; A61K 39/42
(52) U.S. Cl. ................. 435/7.1; 435/5; 435/6; 424/159.1
(58) Field of Search ................ 435/5, 6, 7.1; 424/159.1

(56) References Cited

U.S. PATENT DOCUMENTS

| | | | |
|---|---|---|---|
| 5,420,026 A | 5/1995 | Payne | 435/172.3 |
| 5,571,712 A | 11/1996 | Haynes et al. | 435/240.2 |
| 5,866,320 A | 2/1999 | Rovinski et al. | 435/5 |

OTHER PUBLICATIONS

Genbank Accession No. K03455.
Genbank Accession No. X03633.
Clements, J.E. et al., "Cross–protective Immune Responses Induced in Rhesus Macaques by Immunization with Attenuated Macrophage–Tropic Simian Immunodeficiency Virus." *Journal of virol* 69 (1995): 2737–2744.

Daniel M.D. et al., "Protective Effects of a Live Attenuated SIV Vaccine with a Deletion in the nef Gene." *Science* 258 (1992):1938–1941.

Stahl–Hennig C. et al., "Rapid Development of Faccine Protection in Macaques by Live–Attenuated Simian Immunodeficiency Virus." *Journal of General Virology* 77 (1996): 2969–81.

Norley S. et al., "Protection from Pathogenic SIVmac Challenge Following Short–term Infection with a nef–Deficient Attenuated Virus." *Virology* 219 (1996): 195–205.

Almond N. et al., "Protection by Attenuated Simian Immunodeficiency Virus in Macaques Against Challenge with Virus–Infected Cells."*Lancet* 345 (1995):1342–1344.

Wyand M. et al., "Vaccine Protection by a Triple Deletion Mutant of Simian Immunodeficiency Virus."0 *Journal of Virology* 70 (1996): 3724–3733.

Wyand M. S. et al., "Resistance of Neonatal Monkeys to Live–Attenuated Vaccine Strains of Simian Immunodeficiency Virus." *Nature Medicine* 3 (1997): 32–36.

Baba T. W. et al., "Pathogenicity of Live, Attenuated SIV After Mucosal Infection of Neonatal Macaques." *Science* 267 (1995): 1820–1825.

Cohen, J.,'Weakened SIV Vaccines Still Kills.' *Science* 278 (1997): 24–25.

(List continued on next page.)

Primary Examiner—Hankyel T. Park
(74) Attorney, Agent, or Firm—Kirkpatrick & Lockhart LLP

(57) ABSTRACT

A replication-defective HIV particle pseudotyped with vesicular stomatitis virus G protein (VSV-G). The pol gene of the HIV genome in the particle is modified to inactivate the pol reverse transcriptase and protcase activity. This pseudotyped HIV particle can infect many cell types, including human and simian cells, and only undergoes one round of replication. Furthermore, a virus-specific immune response can be detected in mice immunized with the VSV-G pseudotyped replication-defective HIV.

23 Claims, 6 Drawing Sheets

OTHER PUBLICATIONS

Lu S. et al., "Simian Immunodeficiency Virus DNA Vaccine Trial in Macaques." *Journal of Virology* 70 (1996): 3978–3991.

Gold D., 'Geneva Overview–Vaccines at the 12th World AIDS Conference.' *IAVI Report* 3 (1998): 1+.

Girard M. et al., "Challenge of Chimpanzees Immunized with a Recombinant Canarypox–HIV–1 Virus." *Virology* 232 (1997): 98–104.

Naldini L. et al., "In vivo Gene Delivery and Stable Transduction of Nondividing Cells by a Lentiviral Vector."0 *Science* 272 (1996): 263–267.

Delwart, E. L. et al., "Analysis of HIV–1 Envelope Mutants and Pseudotyping of Replication–Defective HIV–1 Vectors by Genetic Complementation." *Aids Research and Human Retroviruses* 8 (1992): 1669–1677.

Ratner, L. et al., "Complete Nucleotide Sequence of the AIDS Virus, HTLV–III." *Nature* 313 (1985): 277–284.

Chackerian, B., "Human Immunodeficiency Virus Type 1 Coreceptors Participate in Postentry Stages in the Virus Replication Cycle and Function in Simian Immunodeficiency Virus Infection." *Journal of Virology* 71 (1997): 3932–3939.

Tung F. T., Detection of Human Immunodeficiency Virus Type 1 by a Highly Sensitive and Specific Polymerase Chain Reaction Method. *Serodiagnosis and Immunotherapy* 6 (1994): 218–220.

Rinaldo C. et al., "High Levels of Anti–Human Immunodeficiency Virus Type 1 (HIV–1) Memory Cytotoxic T–Lymphocyte Activity and Low Viral Load Are Associated with Lack of Disease in HIV–I Infected Long–term Nonprogressor." *Journal of Virology* 69 (1995): 5838–5842.

Kimpton J. et al. "Detection of Replication–Competent and Pseudotyped Human Immunodeficiency Virus with a Sensitive Cell Line on the Basis of Activation of an Integrated β–Galactosidase Gene." *Journal of Virology* 66 (1992): 2232–2239.

Aiken C., "Pseudotyping Human Immunodeficiency Virus Type 1 (HIV–1) by the Glycoprotein of Vesicular Stomatitis Virus Targets HIV–1 Entry to an Endocytic Pathway and Suppresses Both the Requirement for nef and the Sensitivity to Cyclosporin A. " *Journal of Virology* 71 (1997): 5871–5877.

Miller M.D. et al., "The Gag Specific Cytotoxic T Lymphocyte in Rhesus Monkeys Infected with the Simian Immunodeficiency Virus of Macaques." *Journal of Immunology* 144 (1990): 122–128.

Kent S. J. et al., "Detection of Simian Immunodeficiency Virus (SIV)–specific Cd8+ T Cells in Macaques Protected from SIV Challenge by Prior SIV Subunit Vaccination." *Journal of Virology* 70 (1996): 4941–4947.

Salk J. et al., "A Strategy for Prophylactic Vaccination Against HIV." *Science* 260 (1993): 1270–1272.

Johnson P. R. et al., "Induction of Vigorous Cytotoxic T–Lymphocyte Responses by Live Attenuated Simian Immunodeficiency Virus." *Journal of Virology* 71 (1997): 7711–7718.

D. Trono, M.B. Feinberg, D. Baltimore, *Cell* 59, 113 (1989).HIV–1, pR9.

A. Lever et al., *Journal of Virology* 63 (1989):4085.

SEQUENCE LISTING

<160> NUMBER OF SEQ ID NOS: 1

<210> SEQ ID NO 1
<211> LENGTH: 9719
<212> TYPE: DNA
<213> ORGANISM: Human immunodeficiency virus type 1

<400> SEQUENCE: 1

```
tggaagggct aattcactcc caacgaagac aagatatcct tgatctgtgg atctaccaca      60
cacaaggcta cttccctgat tagcagaact acacaccagg gccagggatc agatatccac     120
tgacctttgg atggtgctac aagctagtac cagttgagcc agagaagtta gaagaagcca     180
acaaaggaga gaacaccagc ttgttacacc ctgtgagcct gcatggaatg gatgacccgg     240
agagagaagt gttagagtgg aggtttgaca gccgcctagc atttcatcac atgcccgag      300
agctgcatcc ggagtacttc aagaactgct gacatcgagc ttgctacaag gactttccg      360
ctggggactt tccagggagg cgtggcctgg gcgggactgg ggagtggcga gccctcagat     420
cctgcatata agcagctgct ttttgcctgt actgggtctc tctggttaga ccagatctga     480
gcctgggagc tctctggcta actagggaac ccactgctta agcctcaata aagcttgcct     540
tgagtgcttc aagtagtgtg tgcccgtctg ttgtgtgact ctggtaacta gagatccctc     600
agaccctttt agtcagtgtg gaaaatctct agcagtggcg cccgaacagg gacctgaaag     660
cgaaagggaa accagaggag ctctctcgac gcaggactcg gcttgctgaa gcgcgcacgg     720
caagaggcga ggggcggcga ctggtgagta cgccaaaaat tttgactagc ggaggctaga     780
aggagagaga tgggtgcgag agcgtcagta ttaagcgggg gagaattaga tcgatgggaa     840
aaaattcggt taaggccagg gggaaagaaa aaatataaat taaaacatat agtatgggca     900
agcagggagc tagaacgatt cgcagttaat cctggcctgt tagaaacatc agaaggctgt     960
agacaaatac tgggacagct acaaccatcc cttcagacag gatcagaaga acttagatca    1020
ttatataata cagtagcaac cctctattgt gtgcatcaaa ggatagagat aaaagacacc    1080
aaggaagctt tagacaagat agaggaagag caaaacaaaa gtaagaaaaa agcacagcaa    1140
gcagcagctg acacaggaca cagcaatcag gtcagccaaa attaccctat agtgcagaac    1200
atccagggc aaatggtaca tcaggccata tcacctagaa ctttaaatgc atgggtaaaa    1260
gtagtagaag agaaggcttt cagcccagaa gtgataccca tgttttcagc attatcagaa    1320
ggagccaccc cacaagattt aaacaccatg ctaaacacag tggggggaca tcaagcagcc    1380
atgcaaatgt taaaagagac catcaatgag gaagctgcag aatgggatag agtgcatcca    1440
gtgcatgcag gcctattgc accaggccag atgagagaac caaggggaag tgacatagca    1500
ggaactacta gtacccttca ggaacaaata ggatggatga caaataatcc acctatccca    1560
gtaggagaaa tttataaaag atggataatc ctgggattaa ataaaatagt aagaatgtat    1620
agccctacca gcattctgga cataagacaa ggaccaaagg aacccttag agactatgta    1680
gaccggttct ataaaactct aagagccgag caagcttcac aggaggtaaa aaattggatg    1740
acagaaacct tgttggtcca aaatgcgaac ccagattgta agactatttt aaaagcattg    1800
ggaccagcgg ctacactaga agaaatgatg acagcatgtc agggagtagg aggacccggc    1860
cataaggcaa gagttttggc tgaagcaatg agccaagtaa caaattcagc taccataatg    1920
atgcagagag gcaatttag gaaccaaaga aagattgtta agtgtttcaa ttgtggcaaa    1980
gaagggcaca cagccagaaa ttgcagggcc cctaggaaaa agggctgttg gaaatgtgga    2040
aaggaaggac accaaatgaa agattgtact gagagacagg ctaattttt agggaagatc    2100
tggccttcct acaagggaag gccagggaat tttcttcaga gcagaccaga gccaacagcc    2160
ccaccagaag agagcttcag gtctggggta gagacaacaa ctccccctca gaagcaggag    2220
ccgatagaca aggaactgta tcctttaact tccctcaggt cactctttgg caacgacccc    2280
tcgtcacaat aaagataggg ggcaactaa aggaagctct attagataca ggagcagatg    2340
atacagtatt agaagaaatg agtttgccag gaagatggaa accaaaaatg atagggggaa    2400
ttggaggttt tatcaaagta agacagtatg atcagatact catagaaatc tgtggacata    2460
aagctatagg tacagtatta gtaggaccta cacctgtcaa cataattgga agaaatctgt    2520
tgactcagat tggttgcact ttaaattttc ccattagccc tattgagact gtaccagtaa    2580
aattaaagcc aggaatggat ggcccaaaag ttaaacaatg gccattgaca gaagaaaaaa    2640
taaaagcatt agtagaaatt tgtacagaga tggaaaagga agggaaaatt tcaaaaattg    2700
ggcctgaaaa tccatacaat actccagtat ttgccataaa gaaaaaagac agtactaaat    2760
ggagaaaatt agtagatttc agagaactta ataagagaac tcaagacttc tgggaagttc    2820
aattaggaat accacatccc gcagggttaa aaaagaaaaa atcagtaaca gtactggatg    2880
tgggtgatgc atatttttca gttcccttag atgaagactt caggaagtat actgcattta    2940
ccatacctag tataaacaat gagacaccag ggattagata tcagtacaat gtgcttccac    3000
agggatggaa aggatcacca gcaatattcc aaagtagcat gacaaaaatc ttagagcctt    3060
ttagaaaaca aaatccagac atagttatct atcaatacat ggatgatttg tatgtaggat    3120
ctgacttaga aatagggcag catagaacaa aaatagagga gctgagacaa catctgttga    3180
ggtggggact taccacacca gacaaaaaac atcagaaaga acctccattc ctttggatgg    3240
gttatgaact ccatcctgat aaatggacag tacagcctat agtgctgcca gaaaaagaca    3300
gctggactgt caatgacata cagaagttag tggggaaatt gaattgggca agtcagattt    3360
acccagggat taaagtaagg caattatgta aactccttag aggaaccaaa gcactaacag    3420
aagtaatacc actaacagaa gaagcagagc tagaactgga gaaaacagag gagattctaa    3480
aagaaccagt acatggagtg tattatgacc catcaaaaga cttaatagca gaaatacaga    3540
agcaggggca aggccaatgg acatatcaaa tttatcaaga gccatttaaa aatctgaaaa    3600
caggaaaata tgcaagaatg aggggtgccc acactaatga tgtaaaacaa ttaacagagg    3660
cagtgcaaaa aataaccaca gaaagcatag taatatgggg aaagactcct aaatttaaac    3720
tgcccataca aaaggaaaca tgggaaacat ggtggacaga gtattggcaa gccacctgga    3780
ttcctgagtg ggagtttgtt aatacccctc ccttagtgaa attatggtac cagttagaga    3840
aagaacccat agtaggagca gaaaccttct atgtagatgg ggcagctaac agggagacta    3900
aattaggaaa agcaggatat gttactaata gaggaagaca aaaagttgtc accctaactg    3960
acacaacaaa tcagaagact gagttacaag caatttatct agctttgcag gattcgggat    4020
```

-continued

```
tagaagtaaa catagtaaca gactcacaat atgcattagg aatcattcaa gcacaaccag    4080
atcaaagtga atcagagtta gtcaatcaaa taatagagca gttaataaaa aaggaaaagg    4140
tctatctggc atgggtacca gcacacaaag gaattgaggg aaatgaacaa gtagataaat    4200
tagtcagtgc tggaatcagg aaagtactat ttttagatgg aaatagataag gcccaagatg    4260
aacatgagaa atatcacagt aattggagag caatggctag tgattttaac ctgccacctg    4320
tagtagcaaa agaaatagta gccagctgtg ataaatgtca gctaaaagga gaagccatgc    4380
atggacaagt agactgtagt ccaggaatat ggcaactaga ttgtacacat ttagaaggaa    4440
aagttatcct ggtagcagtt catgtagcca gtggatatat agaagcagaa gttattccag    4500
cagaaacagg gcaggaaaca gcatattttc ttttaaaatt agcaggaaga tggccagtaa    4560
aaacaataca tactgacaat ggcagcaatt tcaccggtgc tacggttagg ccgcctgtt    4620
ggtgggcggg aatcaagcag gaatttggaa ttccctacaa tccccaaagt caaggagtag    4680
tagaatctat gaataaagaa ttaaagaaaa ttataggaca ggtaagagat caggctgaac    4740
atcttaagac agcagtacaa atggcagtat tcatccacaa ttttaaaaga aaagggggga    4800
ttggggggta cagtgcaggg gaaagaatag tagacataat agcaacagac atacaaacta    4860
aagaattaca aaaacaaatt acaaaaattc aaaattttcg ggtttattac agggacagca    4920
gaaatccact ttggaaagga ccagcaaagc tcctctggaa aggtgaaggg gcagtagtaa    4980
tacaagataa tagtgacata aagtagtgc caagaagaaa agcaaagatc attagggatt    5040
atggaaaaca gatggcaggt gatgattgtg tggcaagtag acaggatgag gattagaaca    5100
tggaaaagtt tagtaaaaca ccatatgtat gtttcaggga aagctagggg atggttttat    5160
agacatcact atgaaagccc tcatccaaga ataagttcag aagtacacat cccactaggg    5220
gatgctagat tggtaataac aacatattgg ggtctgcata caggagaaag agactggcat    5280
ttgggtcagg gagtctccat agaatgagg aaaagagat atagcacaca agtagaccct    5340
gaactagcag accaactaat tcatctgtat tactttgact gttttttcaga ctctgctata    5400
agaaaggcct tattaggaca catagttagc cctaggtgtg aatatcaagc aggacataac    5460
aaggtaggat ctctacaata cttggcacta gcagcattaa taacaccaaa aaagataaag    5520
ccacctttgc ctagtgttac gaaactgaca gaggatagat ggaacaagcc ccagaagacc    5580
aagggccaca gagggagcca cacaatgaat ggacactaga gcttttagag gagcttaaga    5640
atgaagctgt tagacatttt cctaggattt ggctccatgg cttagggcaa catatctatg    5700
aaacttatgg ggatacttgg gcaggagtgg aagccataat aagaattctg caacaactgc    5760
tgtttatcca ttttcagaat tgggtgtcga catagcagaa taggcgttac tcgacagagg    5820
agagcaagaa atggagccag tagatcctag actagagccc tggaagcatc caggaagtca    5880
gcctaaaact gcttgtacca attgctattg taaaaagtgt tgctttcatt gccaagtttg    5940
tttcataaca aaagccttag gcatctccta tggcaggaag aagcggagac agcgacgaag    6000
agctcatcag aacagtcaga ctcatcaagc ttctctatca aagcagtaag tagtacatgt    6060
aacgcaacct ataccaatag tagcaatagt agcattagta gtagcaataa taatagcaat    6120
agttgtgtgg tccatagtaa tcatagaata taggaaaata ttaagacaaa gaaaaataga    6180
caggttaatt gatagactaa tagaaagagc agaagacagt ggcaatgaga gtgaaggaga    6240
aatatcagca cttgtggaga tgggggtgga gatggggcac catgctcctt gggatgttga    6300
tgatctgtag tgctacagaa aaattgtggg tcacagtcta ttatggggta cctgtgtgga    6360
aggaagcaac caccactcta ttttgtgcat cagatgctaa agcatatgat acagaggtac    6420
ataatgtttg ggccacacat gcctgtgtac ccacagaccc caacccacaa gaagtagtat    6480
tggtaaatgt gacagaaaat tttaacatgt ggaaaaatga catggtagaa cagatgcatg    6540
aggatataat cagtttatgg gatcaaagcc taaagccatg tgtaaaatta accccactct    6600
gtgttagttt aaagtgcact gatttgaaga atgatactaa taccaatagt agtagcggga    6660
gaatgataat ggagaaagga gagataatga actgctcttt caatatcagc acaacataa    6720
gaggtaaggt gcagaaagaa tatgcatttt tttataaact tgatataata ccaatagata    6780
atgatactac cagctataag ttgacaagtt gtaacacctc agtcattaca caggcctgtc    6840
caaaggtatc ctttgagcca attcccatac attattgtgc cccggctggt tttgcgattc    6900
taaaatgtaa taataagacg ttcaatggaa caggaccatg tacaaatgtc agcacagtac    6960
aatgtacaca tggaattagg ccagtagtat caactcaact gctgttaaat ggcagtctag    7020
cagaagaaga ggtagtaatt agatctgtca atttcacgga caatgctaaa accataatag    7080
tacagctgaa cacatctgta gaaattaatt gtacaagacc caacaacaat acaagaaaaa    7140
gaatccgtat ccagagagga ccagggagag catttgttac aataggaaata ataggaaata    7200
tgagacaagc acattgtaac attagtagag caaaatggaa taacacttta aaacagatag    7260
ctagcaaatt aagagaacaa tttggaaata taaaacaat aatctttaag caatcctcag    7320
gaggggaccc agaaaattgta acgcacagtt ttaattgtgg aggggaattt ttctactgta    7380
attcaacaca actgtttaat agtacttggt ttaatagtac tggagggtcaa    7440
ataacactga aggaagtgac acaatcaccc tcccatgcag aataaaaacaa attataaaca    7500
tgtggcagaa agtaggaaaa gcaatgtatg cccctcccat cagtggacaa attagatgtt    7560
catcaaatat tacagggctg ctattaacaa gagatggtgg taatagcaac aatgagtccg    7620
agatcttcag acctggagga ggagatatga gggacaattg gagaagtgaa ttatataaat    7680
ataaagtagt aaaaattgaa ccattaggag tagcacccac caaggcaaag agaagagtgg    7740
tgcagagaga aaaaagagca gtgggaatag gagctttgtt ccttgggttc ttgggagcag    7800
caggaagcac tatgggcgca gcctcaatga cgctgacggt acaggccaga caattattgt    7860
ctggtatatg gcagcagcag aacaatttgc tgagggctat tgaggcgcaa cagcatctgt    7920
tgcaactcac agtctgggc atcaagcagc tccaggcaag aatcctggct gtggaaagat    7980
acctaaagga tcaacagctc ctggggattt ggggttgctc tggaaaactc atttgcacca    8040
ctgctgtgcc ttggaatgct agttggagta ataaatctct ggaacagatt tggaatcaca    8100
cgacctggat ggagtgggac agagaaatta acaattacac aagcttaata cactccttaa    8160
ttgaagaatc gcaaaaccag caagaaaaga atgaacaaga attattggaa ttagataaat    8220
gggcaagttt gtggaattgg tttaacataa caaattggct gtggtatata aaattattca    8280
taatgatagt aggaggcttg gtaggtttaa gaatagtttt tgctgtactt tctatagtga    8340
atagagttag gcaggggatat tcaccattat cgtttcagac ccacctccca accccgaggg    8400
gacccgacag gcccgaagga atagaagaag aaggtggaga gagagaccca gacagatcca    8460
ttcgattagt gaacggatcc ttggcactta tctgggacga tctgcggagc ctgtgcctct    8520
tcagctacca ccgcttgaga gacttactct tgattgtaac gaggattgtg gaacttctgg    8580
gacgcagggg gtgggaagcc ctcaaatatt ggtggaatct cctacagtat tggagtcagg    8640
aactaaagaa tagtgctgtt agcttgctca atgccacagc catagcagta gctgagggga    8700
cagatagggt tatagaagta gtacaaggag cttgtagagc tattcgccac atacctagaa    8760
```

-continued

```
gaataagaca gggcttggaa aggattttgc tataagatgg gtggcaagtg gtcaaaaagt  8820
agtgtgattg gatggcctac tgtaagggaa agaatgagac gagctgagcc agcagcagat  8880
agggtgggag cagcatctcg agacctggaa aaacatggag caatcacaag tagcaataca  8940
gcagctacca atgctgcttg tgcctggcta gaagcacaag aggaggagga ggtgggtttt  9000
ccagtcacac ctcaggtacc tttaagacca atgacttaca aggcagctgt agatcttagc  9060
cacttttttaa aagaaaaggg gggactggaa gggctaattc actcccaaag aagacaagat  9120
atccttgatc tgtggatcta ccacacacaa ggctacttcc ctgattagca gaactacaca  9180
ccagggccag gggtcagata tccactgacc tttggatggt gctacaagct agtaccagtt  9240
gagccagata agatagaaga ggccaataaa ggagagaaca ccagcttgtt acaccctgtg  9300
agcctgcatg ggatggatga cccggagaga gaagtgttag agtggaggtt tgacagccgc  9360
ctagcatttc atcacgtggc ccgagagctg catccggagt acttcaagaa ctgctgacat  9420
cgagcttgct acaagggact ttccgctggg gactttccag ggaggcgtgg cctgggcggg  9480
actggggagt ggcgagccct cagatcctgc atataagcag ctgctttttg cctgtactgg  9540
gtctctctgg ttagaccaga tctgagcctg ggagctctct ggctaactag ggaacccact  9600
gcttaagcct caataaagct tgccttgagt gcttcaagta gtgtgtgccc gtctgttgtg  9660
tgactctggt aactagagat ccctcagacc cttttagtca gtgtggaaaa tctctagca   9719
```

REPLICATION DEFECTIVE HIV VACCINE

This application claims the benefit of provisional application Ser. No. 60/085,115 filed May 12, 1998.

BACKGROUND OF THE INVENTION

1. Field of the Invention

A method is described for making a replication-defective HIV virus particle. The present invention is also directed to a HIV virus particle produced according to the method and to a vaccine including the particle.

2. Description of the Related Art

A variety of strategies have evolved in the pursuit of an effective HIV vaccine. One strategy is the use of attenuated viruses. Recent advances in SIV vaccine studies indicate that live attenuated vaccines provide the best protection against challenge with the pathogenic strain of SIV in vaccinated animals (Clements J. E. et al., *Journal of Virology* 69 (1995): 2737–2744; Daniel, M. D. et al., *Science* 258 (1992): 1938–1941; Stahl-Hennig C. et al., *Journal of General Virology* 77 (1996): 2969–2981; Norley, S. et al., *Journal of Virology* 219 (1996): 195–205; Almond, N. et al., *The Lancet* 345 (1995): 1342–1344; Wyand, M. S. et al., *Journal of Virology* 70 (1996): 3724–3733). This animal model suggests that the protective immunity can be elicited by vaccination with attenuated viruses. However, there is a potential risk in using an attenuated virus as a vaccine in humans. This concern is strengthened by studies in which attenuated viruses are shown to cause disease in neonatal rhesus monkeys (Wyand, M. S. et al., *Nature Medicine* 3 (1997): 32–36; Baba, T. W. et al., *Science* 267 (1995): 1820–1825) and, further, by the high rate of reversion of some attenuated SIV strains inoculated in monkeys (Cohen, J., *Science* 278 (1997): 24–25).

Humoral and cellular immune responses can be elicited in rhesus monkeys inoculated with a naked DNA vaccine. However, there is little or no protective immunity observed in vaccinated animals after challenge with SIV (Lu, S. et al., *Journal of Virology* 70 (1996): 3978–3991). The mechanisms of protective immunity elicited by attenuated live vaccines in vaccinated animals have not been identified. Protective immunity may be due to the continuous expression of viral proteins from the persisting viral genome in the vaccinated monkeys, to the expression of all (or part of) the SIV proteins from endogenous pathways, or to other aspects (e.g., viral replication site) of the immune response to the live, attenuated virus.

U.S. Pat. No. 5,571,712, to Haynes et al. discloses replication-defective HIV virus particles which do not include retroviral RNA. These retroviral particles are acceptable for safety reasons due to their inability to replicate. However, these particles differ from vaccines capable of replication in their lesser ability to elicit protective immunity. Thus, it is expected that larger numbers of particles must be administered to a subject in a course of vaccination. Further, lack of expression of viral proteins in a vaccinated subject will affect the quality of the protective immunity.

Other vaccines are currently under development, which include peptide vaccines, DNA vaccines, multi-valent virus (i.e., recombinant canarypox vaccines) and combination vaccines (i.e., a DNA vaccine combined with a fowlpox booster vaccine) with varying results. (Gold, D., *IAVI Report* 3 (1998): 1+.)

The efficacy of HIV vaccines is, generally, difficult to evaluate due to the lack of readily accessible animal models (Girard, M. et al., *Virology* 232 (1997): 98–104). Therefore, it is most desirable to have a replication-defective virus particle with broad tropism, both with regard to range of species it will infect and with regard to the cell types it will infect in a given subject. It is also highly desirable to have a replication-defective virus particle which can produce antigenic HIV proteins in levels and for a duration suitable to elicit a protective immune response, with both cellular and humoral components. These goals have been achieved in the present invention, a replication-defective HIV vaccine pseudotyped with vesicular stomatitis virus G (VSV-G) protein.

SUMMARY OF THE INVENTION

A method is provided for producing a replication-defective retrovirus particle, including the steps of providing a DNA molecule which includes a complete retroviral genome; modifying a portion of the pol gene of the DNA molecule including the protease and reverse transcriptase activity coding regions to the extent that the remaining pol gene cannot produce a protease and reverse transcriptase capable of functioning in replication of the genome, thereby forming a pol$^-$ construct; transferring the pol$^-$ construct into a suitable host cell; prior to, during or after the step of transferring the pol$^-$ construct into the host cell, transferring into the host cell a pseudotyping construct and a packaging construct; growing the host cell under conditions suitable for expression of the constructs and for production of replication-defective retrovirus particles; and collecting the virus particles.

The retroviral genome is preferably an HIV virus genome and most preferably an HIV-1 genome. In one embodiment, the pol$^-$ construct is plasmid pHXB2 with nucleotides 2621–4552 deleted. The method may further include the step of modifying the retroviral genome to represent protein sequence variations in immunologically variant retroviruses.

The pseudotyping construct is preferably a construct for expressing the vesicular stomatitis virus G protein. The pol$^-$ construct, the packaging construct and the pseudotyping construct may be co-transfected or, alternately, at least one of the pseudotyping construct and the packaging construct are carried stably in the genome of the host cell.

The present invention further includes a replication-defective retrovirus particle, including a retroviral genome in which a portion of the pol gene including the protease and reverse transcriptase activity coding regions is modified to the extent that the remaining pol gene cannot produce a protease and reverse transcriptase capable of functioning in replication of the genome. As described above in connection with the method embodiment, the retroviral genome can be an HIV genome and, preferably, an HIV-1 genome. In one embodiment, the retroviral genome is a pol$^-$ construct that is derived from plasmid pHXB2 with nucleotides 2621–4552 thereof deleted. The pseudotyping protein may be the vesicular stomatitis virus G protein.

The present invention further includes a vaccine including the above-described virus particle in its variously described embodiment in combination with a pharmaceutically and/or veterinarilly suitable excipient. The excipient can include mono-, di-, oligo- and polysaccharides, viscosity enhancing and/or tackifying agents, polymers, block polymers and cross-linked polymers. The vaccine can be lyophilized for use in reconstituted form or in immunization by scarification. Further, the vaccine can be formulated into a form selected from the group consisting of an oral liquid, an oral capsule, a liquid for parenteral injection, a transdermal or transmucosal device and a suppository and includes a suitable excipient for preparation of the selected form.

BRIEF DESCRIPTION OF THE DRAWINGS

FIG. 2A shows cells infected with wild-type SIVmac 239, as a positive control; FIG. 2B shows HIVpol$^-$/VSV-G infected cells; and FIG. 2C shows mock-infected cells;

FIG. 5A, lane 1: negative control for PCR (no template DNA), lane 2: mock-transduced CEM174 cells, lane 3: HIVpol$^-$/VSV-G transduced CEM174 cells, lane 4: positive control of PCR (100 pg pHIVpol$^-$), lane 5: positive control of PCR (1 ng of pHIV$_{HXB2}$). A 0.7 kb band indicated the deletion in the pol gene as compared to the wild-type 3 kb band;

FIG. 5B, a nested PCR analysis of DNA extracted from CEM174. Lane 1: negative control of PCR (no template DNA), lane 2: mock transduced cells, lane 3: second round cell-free medium cultured cells, lane 4: HIV$_{IIIB}$-infected cells, and lanes on the right are HIV plasmid DNA with indicated copies number. The one kb fragment indicates the pol gene product. M: 1 kb size marker (BRL/Life Tech.);

DETAILED DESCRIPTION OF THE PREFERRED EMBODIMENTS

Figure 1:
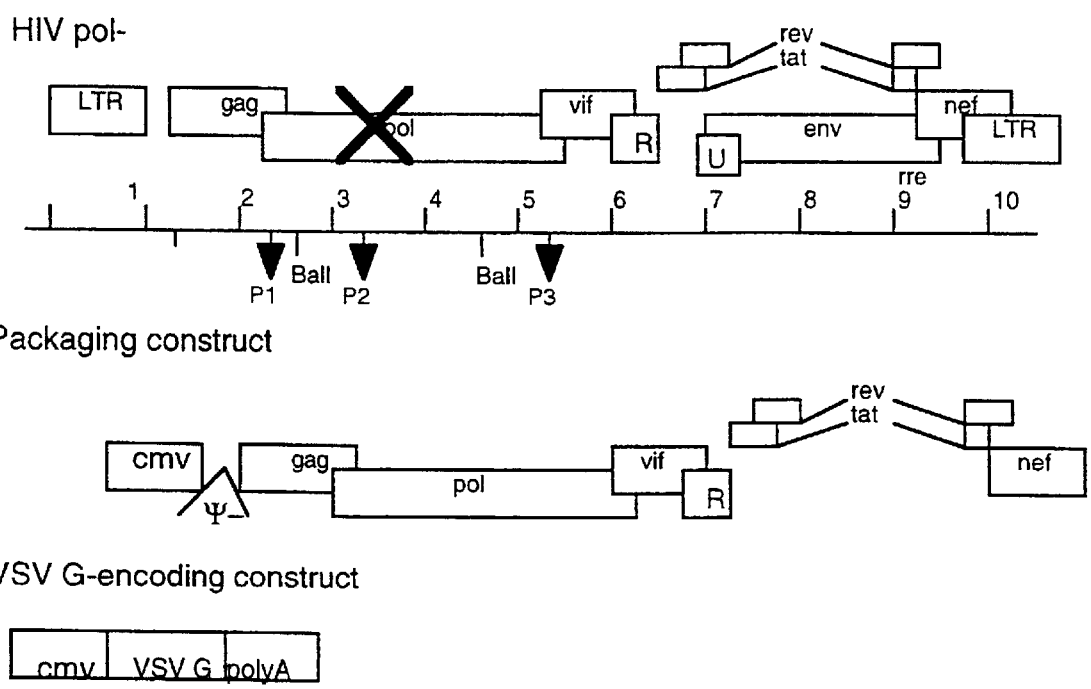
FIG. 1 is a schematic representation of the three plasmid expression system used for generating a VSV-G pseudotyped HIV-1 vector. The BalI restriction site was used to truncate the pol gene. The arrows indicated the primer sites for PCR analysis.

The present invention is a method for producing a replication-defective HIV virus particle, a virus particle prepared according to the method and to a vaccine including the virus particles. The virus particles exhibit increased ability to produce antigen, expanded cell tropism and the ability to elicit strong humoral and cellular immunity. As a result of the expanded tropism, the virus particles can infect rhesus monkeys in a single cycle of replication. Thus, the protective immunity can be further evaluated in rhesus monkeys by challenge with an SIV/HIV chimera virus (SHIV).

The method of the present invention is a method for preparing a replication-defective retroviral particle including the steps of 1) preparing a DNA molecule which includes a complete retroviral genome; 2) modifying a portion of the pol gene including the protease and reverse transcriptase coding regions, to the extent that the remaining pol gene cannot produce a protease and reverse transcriptase capable of functioning in replication of the genome (the pol$^-$ construct); 3) transferring the pol$^-$ construct into a suitable host cell prior to, along with or after the step of transferring a pseudotyping construct and a packaging construct into the host cell or a predecessor cell or a progeny cell thereof; 4) growing the host cell under conditions suitable for expression of the constructs and for production of the replication-defective retrovirus particle; and 5) collecting the virus particles.

The DNA molecule can be prepared from any DNA containing a complete retroviral genome. In theory, a genome suitable for preparing the pol$^-$ construct is any substantially complete retroviral genome which is intact, and encodes and is capable of expressing all viral proteins other than those inactivated by the described modification of the pol gene, whether or not one or more of the viral proteins are modified or unmodified as compared to the wild-type retrovirus. It later may be found that expression of certain viral proteins (non-pol proteins) are unnecessary to elicit protective immunity. A genome having these viral proteins modified or deleted could be a suitable genome for modification according to the methods of the present invention.

According to the present invention, the pol gene of the retroviral genome is modified to cause the protease and the reverse transcriptase functions of the pol gene to lose their viral replication-associated functionality. This loss of function can be induced by a variety of methods, including: by insertions of amino acids, by replacement of amino acids and by deletions of amino acids. Preferably, a significant portion of the pol gene is deleted, as in the example, below.

The packaging construct can be any construct which provides in trans all functions missing from the pol$^-$ construct to allow packaging of the pol$^-$ genome into a replication-defective viral particle which, when transduced, can achieve one round of viral replication. The packaging construct will at least encode a complete and functional reverse transcriptase for incorporation into the replication-defective virus particles and to copy the pol$^-$ genome into DNA once the replication-defective virus particle infects a target cell.

The pseudotyping construct is, preferably, a recombinant construct for expressing the VSV-G protein. Expression of the protein is under transcriptional control of a suitable promoter. In the example below, the common constitutive CMV promoter is used. Other promoters, whether inducible or constitutive, are suitable so long as the construct encodes the VSV-G protein. Alternative pseudotyping proteins may be encoded by and expressed by the pseudotyping construct. An example of an alternative tropism-modifying protein is the Murine Leukemia Virus (MLV) envelope protein. The appropriate pseudotyping protein can be selected according to the application of the vaccine. The VSV-G protein is an appropriate pseudotyping protein for human or simian applications. Different pseudotyping proteins are appropriate for specific veterinary applications, such as if the virus particle is to serve as a Feline Leukemia Virus vaccine.

The host cell for production of replication-defective retrovirus particles can be virtually any mammalian cell so long as the cell is capable of producing infectious virus particles according to the methods described herein. In the examples described below, the preferred, and widely available, 293 cells (human transformed embryonal kidney cells; ATCC CRL-1573, American Type Culture Collection, 12301 Parklawn Drive, Rockville, Md., U.S.A. 20852) are used as host cells to produce the HIV pol$^-$ particles. This cell line is particularly useful due to its ease of growth, its rapid growth characteristics and its ease of transformation by standard protocols. Cells with similar characteristics are particularly suited as host cells for preparation of the replication-defective retrovirus particles.

The example provided below utilizes a three component transfection to produce virus particles. In the example, a first plasmid contains a DNA fragment corresponding to the pol$^-$ HIV genome ("the HIVpol$^-$ construct"). A second plasmid provides suitable functions in trans which are necessary for production of complete retroviral virus particles (the packaging construct). A third plasmid provides the genetic material for expression of the VSV-G protein (a VSV G-encoding or pseudotyping construct). Transfection of the host cell can be accomplished by a variety of methods, including, without limitation: calcium phosphate, liposome and electroporation methods. Virtually any transfection method is suitable, so long as the functionality of each construct is maintained. Further, transfer of the constructs into the host cell can be accomplished simultaneously, or in any desired order.

It should be noted that, although the examples herein utilize plasmid DNA to provide the three constructs, other equivalent vector systems may be utilized to transfer the constructs to the host cell, including, for example and without limitation: linear DNA fragments, plasmids and other recombinant DNA vectors and recombinant virus genomes or particles. In the case of recombinant virus particles, the method for transferring the constructs to the host cell is by transduction with the virus particles. For instance, virus particles including the transfer vectors described in Naldini et al., *Science* 272 (1996): 263–267 would be suitable for delivery of one or both of the packaging construct and the VSV-G-encoding construct. Further, the replication-defective HIV virus particles of the present invention can be used as a suitable source of the particles to transduce the HIV pol$^-$ construct.

Further, a host cell may be established having one or both of the packaging construct and the pseudotyping construct integrated permanently into the host cell DNA. Packaging cell lines for retroviruses are well known in the art. (Delwart, E. L. et al., *Aids Research and Human Retroviruses* 8 (1992): 1669–1677). The integrated packaging construct and pseudotyping construct may be under the control of a constitutive promoter such as the cytomegalovirus (CMV) promoter, as described in the examples, or under the control of an inducible promoter, allowing exact control of virus production and preventing interference with host cell growth during passage of the packaging cell line. Transfection inefficiencies are lessened by the integration of one or more of the constructs into the host cell genome.

Virus particles prepared according to the above-described method include all components of a wild-type virus particle with the exception that the particles include, at least, the above-described modified (pol$^-$ retroviral) genome, as opposed to the wild-type RNA genome. Further, the virus particles preferably include the VSV-G (pseudotyping) protein in order to alter the tropism of the virus particles. Virus particles are prepared according to the above-described methods and are, then, collected by standard methodology.

In the example provided herein, the virus particles are purified by sucrose gradient ultracentrifugation. Other methods for purification can be employed, such as affinity chromatography, so long as the method enables concentrate of the titer of the infectious replication-defective virus particles.

In use, the replication-defective HIV virus particles are formulated as a vaccine. The only limitation is that the vaccine includes, in addition to the virus particles a pharmaceutically or veterinarilly acceptable excipient, which can include, without limitation: virus stabilizing compounds (i.e., sugars such as sucrose or other saccharides or polysaccharides); buffer systems (i.e., TNE or its equivalents); antibiotic compounds (i.e., bacteriocides, bacteriostatic agents and fungicides); viscosity enhancing agents (i.e., polyethylene glycol); polymeric materials (i.e., polymers, copolymers, block polymers and cross-linked polymers) for use as viscosity enhancing agents, as tackifying agents or as a matrix or reservoir for harboring the particles; tackifying agents which promote adhesion of the vaccine mixture to the skin or mucosa; viral transduction-enhancing agents; penetration enhancing agents; flavoring agents; coloring agents; adsorption enhancing agents and adjuvants. For example, as shown below, mice were immunized with virus particles in tissue culture media, which served as a suitable excipient.

The vaccine can be prepared in many forms (and with an excipient suitable for each form), such as, without limitation: an oral liquid for either swallowing or for application to a surface of the mouth, including sublingual or buccal application; an oral capsule or tablet; a liquid for parenteral injection; a cream or ointment for topical application; a lyophilized product for reconstitution or for vaccination by scarification; a transdermal preparation; and a liquid or a suppository for rectal or intravaginal application. A "lyophilized product" is understood to include virus particles freeze-dried, lyophilized or vitrified in the presence of a suitable buffer system, such as TNE, and a suitable carrier, such as a sugar (i.e., trehalose or sucrose), a polysaccharide, or other compounds suitable for stabilizing labile biological compounds.

The vaccine can also contain two or more pol$^-$ variants of the same retrovirus. Therefore, a subject can be immunized once or multiple times with two or more variants of the virus which reflect common antigenic variations of HIV. Production of a variant virus would be straight-forward once the nucleotide sequence of the variant HIV is known. Appropriate modification of DNA encoding the replication-defective genome would be accomplished through well known cloning and mutagenesis methods.

EXAMPLE

A. Materials and Methods

1. Plasmid Constructs and Virus Production

An HIV-1 genome with a deletion in the Pol gene was constructed by deleting a 1.9 kb BalI fragment (2621–4552 nt) of molecular clone pHXB2 (Ratner L. et. al, *Nature* 313 (1985): 277–284, GeneBank No. K03455). The resulting plasmid is called pHIVpol$^-$. A helper expression vector (pCMVΔR8.2) encoding HIV-1 gag and pol genes was obtained. The packaging sequence (ψ) and long terminal repeat (LTR) of HIV-1 were deleted from this expression vector. Therefore, the viral RNA transcribed from this expression vector cannot be packaged into viral particles.

Plasmid pCMVΔR8.2 was constructed from an infectious molecular clone of proviral HIV-1, pR9 (D. Trono, M. B. Feinberg, D. Baltimore, Cell 59, 113, 1989). A 1.3 K base pair BglII fragment (6308≧7611) was deleted from the envelope gene. A 39 base pair internal deletion in the packaging signal sequence was introduced (A. Lever et al., Journal of Virology 63 (1989): 4085), and the 3'HIV long terminal repeat (LTR) was replaced with poly-A site of insulin genomic DNA. The 5'LTR and leader sequence of HIV were substituted with a 0.8 K base pair fragment containing the CMV promoter (Naldini, *Science* 272 (1996): 263–268).

A VSV-G protein expression construct (pCMV.VSV.G) was obtained. Plasmid pCMV.VSV.G was constructed by inserting a 1.7 k base pair fragment encoding the VSV.G protein (GeneBank No. XO3633) into the BamHI site of pCMVneo.

The pseudotyped virus was produced by co-transfecting these three plasmids into a highly transfectable cell line 293T, as shown in FIG. 1. About $10^6$ 293T cells were transfected with 5 μg of each plasmid by the calcium phosphate method. Seventy-two hours after transfection, cell-free virus supernatant ("HIVpol⁻/VSV-G") was harvested and stored at −80° C. Some viruses were concentrated by sucrose density gradient ultracentrifugation at 100,000×g for 2 hours and were resuspended into TNE buffer (50 mM Tris.HCl pH 7.8, 130 mM NaCl, 1 mM EDTA). The viral titer was determined on MAGI and sMAGI cells as described. In brief, cells were transduced with serial dilutions of viruses and stained with 5-bromo-4-chloro-3-indolyl-β-D-galactopyranoside (X-Gal) after 3 days of incubation.

2. Transduction of sMAGI Cell Line

An indicator cell line, sMAGI (Chackerian, B. et al., *Journal of Virology* 71 (1997): 3932–3939), was used for the transduction assays. sMAGI cells are derived from macaque mammary tumor cells. They express human CD4 and encode an HIV LTR fused to the β-galactosidase (β-Gal) reporter gene. This cell line allows detection of productive infection by a single virus particle by exploiting the ability of the SIV or HIV Tat protein to transactivate the β-Gal gene through the HIV LTR promoter. sMAGI cells were transduced with one ml of 1:1 medium-diluted virions in the presence of 8 μg/ml of polybrene. Transduced cells were incubated for 3 days at 37° C. before X-Gal staining.

3. Immunoprecipitation

Approximately $10^6$ 293T cells were transduced with $10^5$ transducing units/ml HIVpol⁻/VSV-G. Forty-eight hours later, transduced cells were labeled with $^{35}S$ methionine for 16 hours. A cellular lysate of transduced cells was immunoprecipitated with anti-HIV serum from AIDS patients. For analysis of pseudotyped virus particles, $10^6$ 293T cells were transfected with three plasmids (pHIVpol⁻, pCMVΔR8.2, and pVSV-G) or two plasmids (without pVSV-G). Twenty-four hours later, transfected cells were labeled with $^{35}S$ methionine for 16–24 hours. The cell-free medium was then immunoprecipitated with anti-HIV serum.

4. PCR Analysis

Total DNA was extracted from about $10^5$ CEM174 cells transduced with 1 ml of cell-free virus and subjected to PCR analysis of the pol gene with primers P1 and P3 (see FIG. 1). To monitor the replication-competent virus in the virus preparation, the cell-free medium harvested from one week culture of the transduced CEM174 cells was used to culture CEM174 cells again for another week. The total DNA was isolated from the second CEM174 cell culture and was subjected to a sensitive nested PCR analysis of pol gene with primers P1 and P2 (Tung, F. T., *Serodiagnosis and Immunotherapy* 6 (1994): 218–220).

5. Cytotoxic T Lymphocyte Assay

Immortalized B cells from HIV infected individuals were transduced with HIVpol⁻/VSV-G at MOI=0.1 and used as target cells in a standard chromium release assay (Rinaldo, C. et al., *Journal of Virology* 69 (1995): 5838–5842). B cells infected with vaccinia virus vectors (MOI=5) expressing HIV-1 proteins were used as a control. Different ratios of effector cells were added to $10^4$ B cells for each assay.

6. Immunization of Mice

BALB/c mice were immunized intramuscularly with 0.1 ml (approximately 20 ng of p24) of cell-free pseudotyped viral supernatant (titer of $10^5$ transducing units TU/ml) at 7–10 day intervals for a total of 5 times. Sera were collected (retro-orbital venous plexus during Metophane-induced anesthesia) and tested (1:100 dilution) using an HIV-1 Western blot kit (BioRad, Calif.). Prebleed mouse sera and HIV seropositive sera were used as controls. Alkaline phosphatase conjugated goat anti-mouse antibody (Sigma, St. Louis, Mo.) was used as the second antibody for mouse serum samples. Alkaline phosphatase conjugated goat anti-human antibody (included in the kit) was used as the second antibody for positive control.

B. Results

1. Construction of Plasmid pHIVpol⁻ pHIVpol⁻ was constructed by deleting a 1.9 kb BalI fragment of the pol gene of an HIV-1 genome and was self-ligated by T4 ligase. pHIVpol⁻ encodes all HIV-1 genes including a truncated pol gene. This construct cannot generate infectious viruses when transfected into CEM174 cells (data not shown).

2. Production of Replication-defective HIV

Figure 2A:
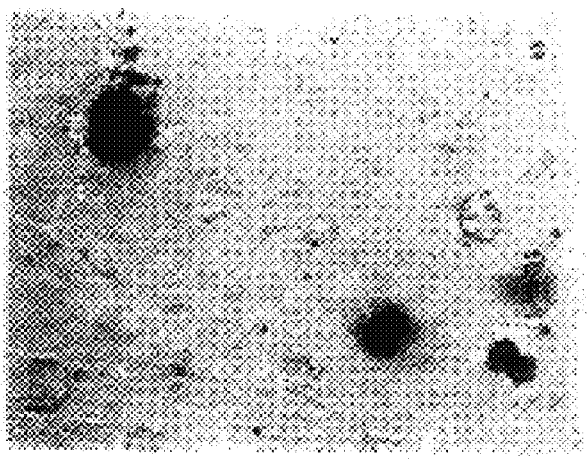
FIGS. 2A–C are micrographs showing transduction of sMAGI cells with HIVpol$^-$/VSV-G. Three days after transduction, cells were stained with X-gal.
Figure 2B:
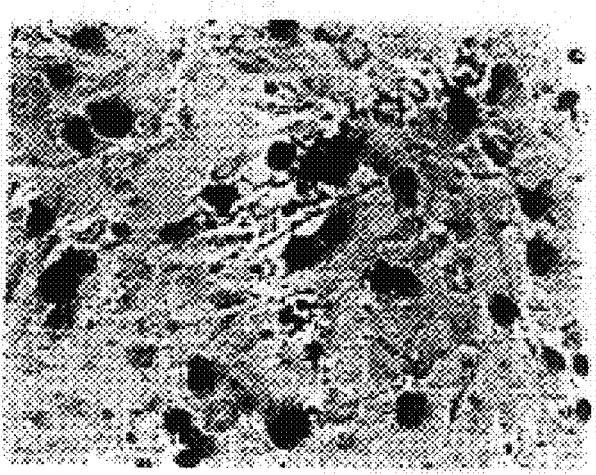
Figure 2C:
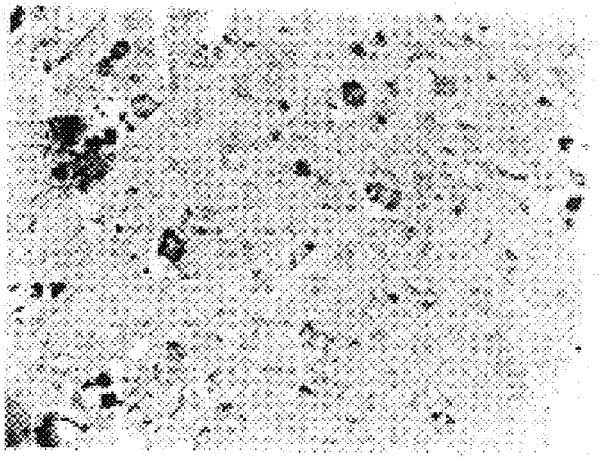

Cell-free virus stocks were produced by co-transfecting three plasmids (or without pVSV-G) into a highly transfectable cell line 293T (FIG. 1). The cell-free viruses were then used to transduce sMAGI cells to assess virus infectivity. The sMAGI cells can only be infected with SIV; none of the HIV-1 strains (macrophage or T-cell tropic) tested to date can establish productive infection (data not shown) (Chackerian, B.: 3932–3939) The HIVpol⁻/VSV-G produced from co-transfection of the three plasmids can infect sMAGI, as shown in FIGS. 2A–C. When any one of the three plasmids was omitted in co-transfection to produce pseudotyped virus, no productive infection was established in sMAGI cells (data not shown).

3. The Titer of HIVpol⁻/VSV-G Can Be Concentrated by Ultracentrifugation

The titer of HIVpol⁻/VSV-G was determined on sMAGI and MAGI cells (Table 1). Like sMAGI cells, MAGI cells were derived from human HeLa CD4 cells encoding an LTR-driven β-gal gene (Kimpton, J. et al., *Journal of Virology* 66 (1992): 2232–2239). A viral titer of 2–4×$10^5$ transduction units/ml, which is higher than that of HIV-1 cultured in CEM cells, can be prepared routinely from transient transfected cells without concentration. Virus particles can be concentrated by sucrose density gradient ultracentrifugation without losing infectivity (>95% recovery). The virus was quite stable even after two freeze-thaw cycles.

TABLE 1

Viral titer of HIVpol⁻/VSV-G on sMAGI and MAGI cells.

| Freeze-thaw cycle | Unconcentrated virus | | Concentrated virus (30-fold) | |
|---|---|---|---|---|
| | sMAGI | MAGI | sMAGI | MAGI |
| 1 | 4 × $10^5$ | 4 × $10^5$ | 9 × $10^6$ | 1 × $10^7$ |
| 2 | 2 × $10^5$ | 3 × $10^5$ | ND | ND |

Abbreviation: ND, Not determined

4. The Formation of Pseudotyped Viral Particles

Figure 3:
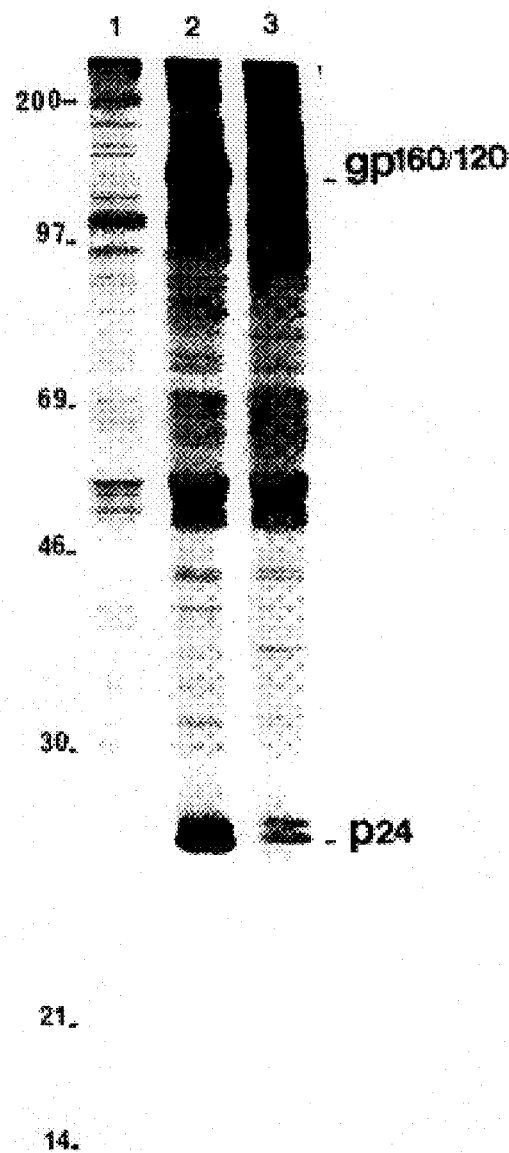
FIG. 3 is an autoradiograph of the immunoprecipitation of pseudotyped viruses. $^{35}$S labeled cell-free viruses were immunoprecipitated with anti-HIV-1 serum. Lane 1: mock-transfected cells, lane 2: cells transfected with pHIVpol$^-$ and pCMVΔR8.2 constructs, lane 3: cells transfected with three plasmids. Molecular weight markers are indicated on the left.

To confirm the formation of pseudotyped virus, the HIVpol⁻/VSV-G pseudotyped viral particles were analyzed by immunoprecipitation. About $10^6$ 293T cells were co-transfected with the three plasmids (or without pVSV-G). The transfected cells were labeled with $^{35}S$ methionine for 24 hours. Cell-free medium was immunoprecipitated with anti-serum from an AIDS patient. The results indicated that both the HIV-1 gag and env were precipitated with anti-HIV-1 antiserum in pseudotyped and non-pseudotyped viruses (FIG. 3). However, in the presence of VSV-G protein, fewer env proteins were precipitated, suggesting that VSV-G protein is competing with env for incorporation into the pseudotyped viruses.

5. Transduction of HIVpol⁻/VSV-G into CD4 and Non-CD4 Cells

Figure 4:
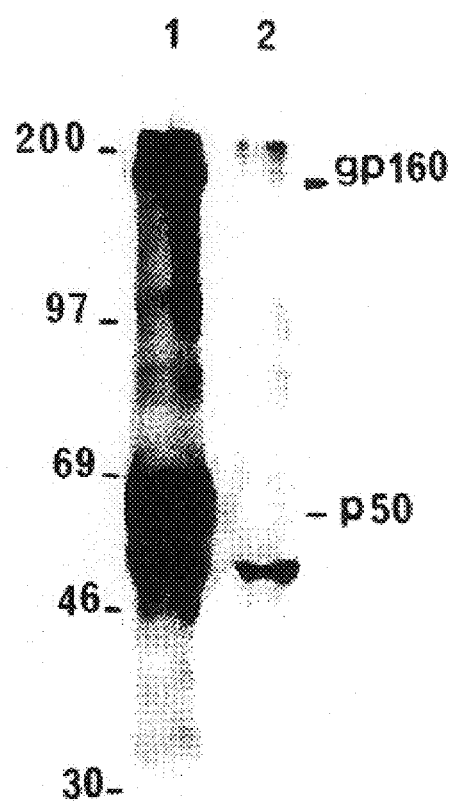
FIG. 4 is autoradiograph of the immunoprecipitation of 293T cells transduced with HIVpol$^-$/VSV-G. Transduced (lane 1) and untransduced (lane 2) 293 T cells were immunoprecipitated with anti-HIV-1 serum.

To confirm that HIVpol⁻/VSV-G can express HIV-1 genes in transduced cell lines, HeLa-CD4 clone 1022 (CD4⁺) and 293T(CD4⁻) cells were transduced with HIVpol⁻/VSV-G. Significant numbers of multinuclear syncytia were observed in HeLa-CD4 clone 1022 cells 48 hours after transduction with HIVpol⁻/VSV-G (data not shown), suggesting a high level of env expression. The expression of HIVpol⁻/VSV-G transduced HIV genes was further analyzed by immunoprecipitation in 293T cells. The results indicated that gag (p50, precursor Gag) and env (gp160/120) proteins were detected in the pseudotyped virus-transduced 293T cells (FIG. 4). The gag cannot be processed into p24 and p17 because no viral protease activity is present in the HIVpol⁻/VSV-G transduced 293T cells.

6. PCR Analysis of Transduced Cells and Replication-competent Virus

Figure 5A:
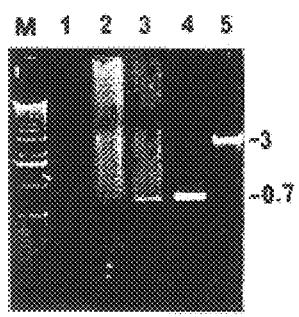
FIGS. 5A and 5B are photographs of agarose gels showing PCR analysis of HIVpol$^-$/VSV-G transduced CEM174 cells. CEM174 cells were transduced with HIVpol$^-$/VSV-G (FIG. 5A) or were cultured with second round cell-free medium (FIG. 5B)
Figure 5B:
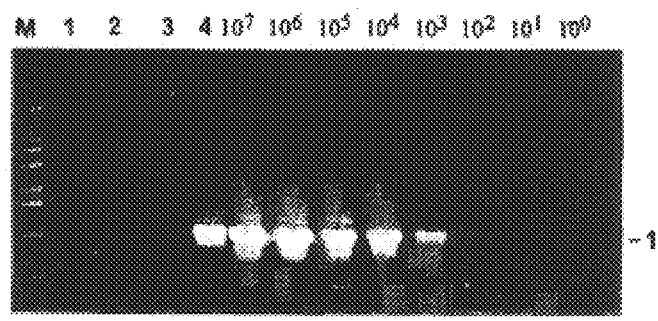

To further verify the presence of HIV-1 genes in the pseudotyped virus-transduced cells, PCR analysis of total DNA isolated from HIVpol⁻/VSV-G transduced CEM174 cells was positive for the truncated pol gene (FIG. 5A). A 0.7 kb PCR fragment indicated the cells were transduced with the pol deletion virus. To demonstrate the absence of replication-competent virus in the pseudotyped virus preparation, cell-free culture medium from a one-week culture of the transduced CEM174 cells was used to culture CEM174 cells for another week. The two-week culture medium was checked for p24 and for reverse transcriptase activity. The results indicated no viral activity in the two-week culture medium. The CEM174 cells from the two-week culture were also checked for provirus sequence by a sensitive nested PCR. This nested PCR can detect less than 10 copies of provirus. The results indicated that no provirus was detected in the second round of infection, suggesting no replication-competent virus in the viral preparation (FIG. 5B).

Figure 6:
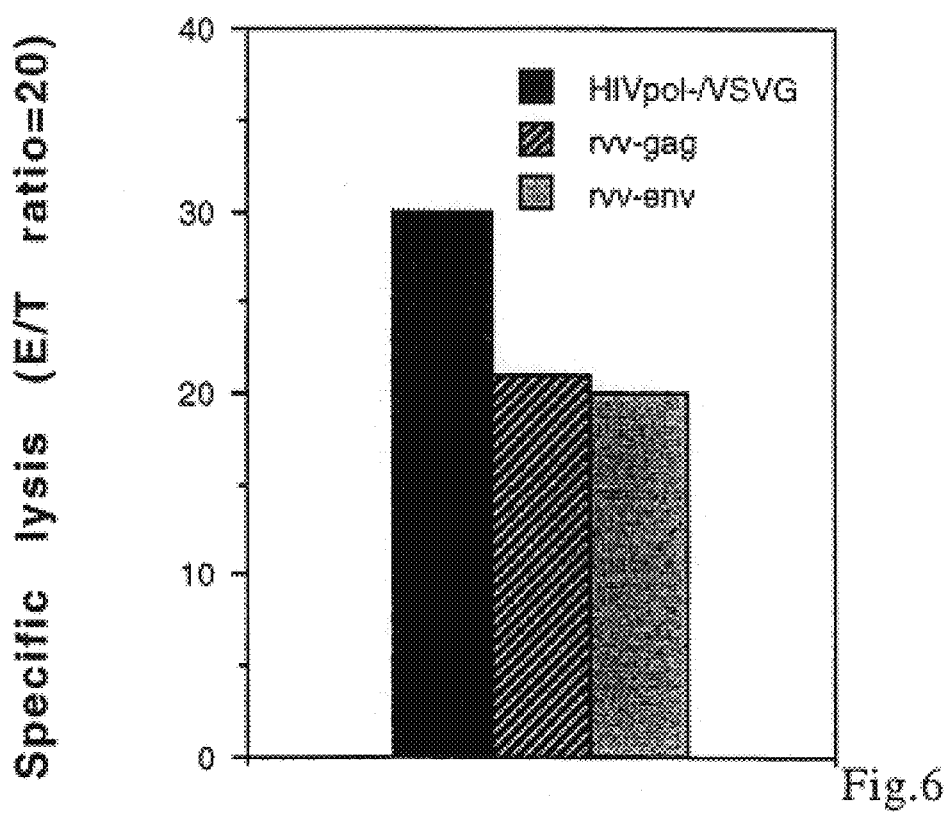
FIG. 6 is a graph showing the results of a standard chromium release assay. Autologous B cells from HIV infected individuals were infected with HIVpol$^-$/VSV-G (MOI=0.1) or vaccinia vectors expressing gag (rVV-gag) or env (rVV-env) genes (MOI=5) as target cells one day before assay.

7. HIV Pseudotyped Virus Transduced B Cells Can Function as Target Cells for Cytotoxic T Lymphocytes To check the HIV-1 protein expression in pseudotyped virus transduced primary cells, immortalized B cells from AIDS patients were transduced with HIVpol⁻/VSV-G and were used as target cells in a standard chromium release assay. Autologous T cells recognized and lysed the HIVpol⁻/VSV-G transduced B cells with an efficiency equal to (or better than) B cells infected with vaccinia vectors expressing HIV-1 genes (FIG. 6). Thirty percent specific lysis was observed at the effector-to-target cell ratio of 20:1. These data suggest that the HIV-1 protein can be expressed and processed normally in transduced primary B cells.

8. Antibody Responses in Immunized Mice

Figure 7:
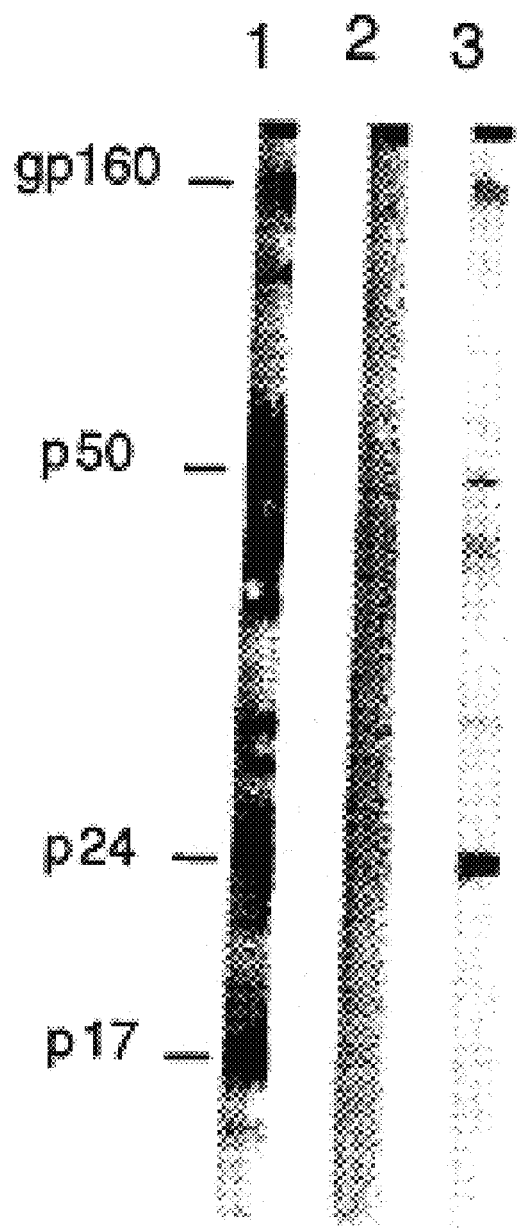
FIG. 7 is a photograph of a Western blot analysis showing antibody responses in mice immunized with VSV-G pseudotyped HIVpol$^-$ viruses. Lane 1: positive control, lane 2: prebleed sera, and lane 3: representative of immunized mice sera.

To demonstrate the immunogenicity of pseudotyped viruses, BALB/c mice were immunized with cell-free viruses and antibody responses were checked by Western blot. The results indicated that weak but clearly visible bands appeared in Western blot assay (FIG. 7). Three major viral proteins (p24, p50 and gp160) were detected two months after immunization. Prebleed sera were negative. These data indicated that cell-free viral supernatant is immunogenic in the vaccinated mice.

Lyophilization

Cell-free virus supernatant (HIVpol⁻/VSV-G) was prepared as described above, in 293T cells in DMEM with 10% fetal bovine serum. One (1) ml of cell-free culture supernatant was dispensed into a 1.5 ml plastic tube and the sample was stored for about two months at −80° C. The frozen sample containing the pseudotyped virus particles was placed into a standard SpeedVac connected to a vacuum pump. The sample was dried in the SpeedVac for one hour under a vacuum. The lyophilized sample was assayed for infectivity as described above. Substantial virus infectivity was retained in the lyophilized sample.

This data indicates that the pseudotyped virus particles are exceptionally stable as compared to native retrovirus particles. Further, typical retrovirus particles do not retain substantial infectivity after sucrose density gradient ultracentrifugation. That the pseudotyped virus particles survive both ultracentrifugation and lyophilization is unexpected and indicates that the HIVpol⁻/VSV-G is a superior vaccine product.

The described replication-defective HIV-1 vector can establish only a single cycle of viral replication. Viral antigens were expressed in transduced cells and functioned as target cells for cytotoxic T lymphocytes from HIV infected individuals. Furthermore, an antibody response to HIV-1 has been demonstrated in mice immunized with the described replication-defective HIV.

The replication-defective HIV-1 described herein provides a safe vaccine. The replication defective virus presented herein encodes all HIV-1 proteins and a truncated pol gene. Because the important protease and reverse transcriptase activities are nonfunctional in the described construct, provirus cannot initiate a second round of replication. The VSV-G pseudotyped virus expands cell tropism to all primate species as well as expanding the types of cells which may be infected in a single animal or individual. Therefore, the safety and efficacy of the same vaccine preparations can be evaluated in monkeys, chimpanzees and humans. A recent report indicates that VSV-G pseudotyped HIV-1 not only can expand cell tropism but also can enhance infectivity by using a different receptor pathway (Aiken, C., *Journal of Virology* 71 (1997): 5871–5877). A unique feature of the replication-defective retroviral vector described herein is the absence of co-expression of foreign protein derived from the vector systems (e.g., adenovirus, poliovirus and vaccinia virus vectors) during the single round of replication. Therefore, an advantage over the attenuated retroviral and pox vaccines is that it is feasible to repeatedly immunize a subject in order to boost the immune response.

It is believed that cell-mediated immunity plays a very important role in protective immunity of viral infection and is associated with long-term survival of HIV-1 infected patients (Miller, M. D. et al., *Journal of Immunology* 144 (1989): 122–128; Kent, S. J. et al., *Journal of Virology* 70 (1996): 4941–4947). The class-I restricted antigen presenting pathway is responsible for cell-mediated immunity (Salk, Jonas et al., *Science* 260 (1993): 1270–1272). It has been demonstrated that the live attenuated vaccines provided the best protective immunity against SIV infection in vaccinated animals. In that system, the protective immunity could be elicited due to cell-mediated immune response as the result of endogenously expressed viral antigens (Johnson, R. P. et al., *Journal of Virology* 71 (1997): 7711–7718). The replication-defective HIV-1 vector described herein provides a safe vaccine candidate to express viral antigens endogenously. Despite the low MOI (0.1) of defective HIV that was used in the cytotoxic T lymphocyte assay, strong (30%) specific lysis was observed in the chromium release assay. These data suggest either high level of viral protein expression or high efficiency of transduction in primary B lymphocytes. Furthermore, the efficacy of protective immunity can be further tested in the rhesus monkeys and in other nonhuman primates.

It is not clear which viral antigen elicits the protective immunity in attenuated viruses vaccinated animals. Using replication-defective HIV-1 vectors with different deletions (e.g., gag, gag-pol, env), the viral factors contributing to the protective immunity (cellular or humoral immune responses) can be assessed in this system. Because viral antigens (about 200 ng/ml p24) are present in the viral supernatants used for the immunization, it is not absolutely certain whether the antibody response elicited in mice is due to soluble viral antigens or endogenously expressed viral proteins. Due to the fact that no adjuvant was used for immunization and little (total of 100 ng p24 per mouse) viral supernatant (antigens) was inoculated into the mice, the antibody responses were likely elicited by the transduced cells.

It is intriguing and unexpected that defective HIV particles cannot establish productive infection in MAGI cells when the VSV-G protein is omitted from the viral particles. Since all the viral structure proteins are present in the co-transfected cells, this phenomenon suggests that VSV-G protein is much more efficient than envelope protein for viral infectivity in this assay system.

The above invention has been described with reference to the preferred embodiment. Obvious modifications and alterations will occur to others upon reading and understanding the preceding detailed description. It is intended that the invention be construed as including all such modifications and alterations insofar as they come within the scope of the appended claims or the equivalents thereof.

REFERENCES

1. Clements J. E. et al., "Cross-protective Immune Responses Induced in Rhesus Macaques by Immunization with Attenuated Macrophage-Tropic Simian Immunodeficiency-Virus." *Journal of Virol* 69 (1995): 2737–2744.
2. Daniel M. D. et al., "Protective Effects of a Live Attenuated SIV Vaccine with a Deletion in the nef Gene." *Science* 258 (1992): 1938–1941.
3. Stahl-Hennig C. et al., "Rapid Development of Vaccine Protection in Macaques by Live-Attenuated Simian Immunodeficiency Virus." *Journal of General Virology* 77 (1996): 2969–81.
4. Norley S. et al., "Protection from Pathogenic SIVmac Challenge Following Short-term Infection with a nef-Deficient Attenuated Virus." *Virology* 219 (1996): 195–205.
5. Almond N. et al., "Protection by Attenuated Simian Immunodeficiency Virus in Macaques Against Challenge with Virus-Infected Cells." *Lancet* 345 (1995): 1342–1344.
6. Wyand M. et al., "Vaccine Protection by a Triple Deletion Mutant of Simian Immunodeficiency Virus." *Journal of Virology* 70 (1996): 3724–3733.
7. Wyand M. S. et al., "Resistance of Neonatal Monkeys to Live Attenuated Vaccine Strains of Simian Immunodeficiency Virus." *Nature Medicine* 3 (1997): 32–36.
8. Baba T. W. et al., "Pathogenicity of Live, Attenuated SIV After Mucosal Infection of Neonatal Macaques." *Science* 267 (1995): 1820–1825.
9. Cohen J., "Weakened SIV Vaccines Still Kills." *Science* 278 (1997): 24–25.
10. Lu S. et al., "Simian Immunodeficiency Virus DNA Vaccine Trial in Macaques." *Journal of Virology* 70 (1996): 3978–3991.
11. Gold, D., "Geneva Overview-Vaccines at the 12th World AIDS Conference." *IAVI Report* 3 (1998): 1+.
12. Girard M. et al., "Challenge of Chimpanzees Immunized with a Recombinant Canarypox-HIV-1 Virus." *Virology* 232 (1997): 98–104.
13. Naldini L. et al., "In Vivo Gene Delivery and Stable Transduction of Nondividing Cells by a Lentiviral Vector." *Science* 272 (1996): 263–267.
14. Delwart, E. L. et al., "Analysis of HIV-1 Envelope Mutants and Pseudotyping of Replication-Defective HIV-1 Vectors by Genetic Complementation." *Aids Research and Human Retroviruses* 8 (1992): 1669–1677.
15. Ratner, L. et al., "Complete Nucleotide Sequence of the AIDS Virus, HTLV-III." *Nature* 313 (1985): 277–284.
16. Chackerian B., "Human Immunodeficiency Virus Type 1 Coreceptors Participate in Postentry Stages in the Virus Replication Cycle and Function in Simian Immunodeficiency Virus Infection." *Journal of Virology* 71 (1997): 3932–3939.
17. Tung F. T., "Detection of Human Immunodeficiency Virus Type 1 by a Highly Sensitive and Specific Polymerase Chain Reaction Method." *Serodiagnosis and Immunotherapy* 6 (1994): 218–220.
18. Rinaldo C et al., "High Levels of Anti-Human Immunodeficiency Virus Type 1(HIV-1) Memory Cytotoxic T-Lymphocyte Activity and Low Viral Load Are Associated with Lack of Disease in HIV-i Infected Long-term Nonprogressor." *Journal of Virology* 69 (1995): 5838–5842.
19. Kimpton J. et al., "Detection of Replication-Competent and Pseudotyped Human Immunodeficiency Virus with a Sensitive Cell Line on the Basis of Activation of an Integrated β-Galactosidase Gene." *Journal of Virology* 66 (1992): 2232–2239.
20. Aiken C., "Pseudotyping Human Immunodeficiency Virus Type 1 (HIV-1) by the Glycoprotein of Vesicular Stomatitis Virus Targets HIV-1 Entry to an Endocytic Pathway and Suppresses Both the Requirement for nef and the Sensitivity to Cyclosporin A." *Journal of Virology* 71 (1997): 5871–5877.
21. Miller M. D. et al., "The Gag Specific Cytotoxic T Lymphocyte in Rhesus Monkeys Infected with the Simian Immunodeficiency Virus of Macaques." *Journal of Immunology* 144 (1990): 122–128.
22. Kent S. J. et al., "Detection of Simian Immunodeficiency Virus (SIV)-specific Cd8+ T Cells in Macaques Protected from SIV Challenge by Prior SIV Subunit Vaccination." *Journal of Virology* 70 (1996): 4941–4947.
23. Salk J. et al., "A Strategy for Prophylactic Vaccination Against HIV." *Science* 260 (1993): 1270–1272.
24. Johnson P. R. et al., "Induction of Vigorous Cytotoxic T-Lymphocyte Responses by Live Attenuated Simian Immunodeficiency Virus." *Journal of Virology* 71 (1997): 7711–7718.

I claim:

1. A method for producing replication-defective retrovirus particles, comprising the steps of:
   a. providing a DNA molecule which includes a complete retroviral genome;
   b. modifying a portion of the pol gene of the DNA molecule including the protease and reverse transcriptase activity coding regions to the extent that the remaining pol gene cannot produce a protease and reverse transcriptase functioning in replication of the genome, thereby forming a pol⁻ construct;
   c. transferring the pol⁻ construct into a suitable host cell;
   d. prior to, during or after the step of transferring the pol⁻ construct into the host cell, transferring into the host cell or a predecessor cell or a progeny cell thereof, a pseudotyping construct and a packaging construct;
   e. growing the host cell under conditions suitable for expression of the constructs and for production of the replication-defective retrovirus particles; and
   f. collecting the replication-defective virus particles.

2. The method for producing replication-defective retrovirus particles as claimed in claim 1, wherein the retroviral genome is an HIV virus genome.

3. The method for producing replication-defective retrovirus particles as claimed in claim 1, wherein the retroviral genome is an HIV-1 virus genome.

4. The method for producing replication-defective retrovirus particles as claimed in claim 3, wherein the pol gene is modified by deleting a portion thereof.

5. The method for producing replication-defective retrovirus particles as claimed in claim 1, wherein the pol⁻ construct is plasmid pHXB2 with nucleotides 2621–4552 thereof deleted.

6. The method for producing replication-defective retrovirus particles as claimed in claim 1, wherein the retroviral genome is a Feline Leukemia Virus genome.

7. The method for producing replication-defective retrovirus particles as claimed in claim 1, further comprising the step of modifying the retroviral genome to represent protein sequence variations in immunologically variant retroviruses.

8. The method for producing replication-defective retrovirus particles as claimed in claim 3, wherein the pseudotyping construct encodes the vesicular stomatitis virus G protein.

9. The method for producing replication-defective retrovirus particles as claimed in claim 1, wherein at least one of the pol⁻ construct, the pseudotyping construct and the packaging construct are co-transfected.

10. The method for producing replication-defective retrovirus particles as claimed in claim 1, wherein the collecting step includes a step of concentrating the titer of the replication-defective virus particles.

11. A replication-defective retrovirus particle, comprising:
    a. a retroviral genome in which a portion of the pol gene including the protease and reverse transcriptase activity coding regions is modified to the extent that the remaining pol gene cannot produce a protease and reverse transcriptase functioning in replication of the genome; and
    b. a pseudotyping protein.

12. The replication-defective retrovirus particle as claimed in claim 11, wherein the retroviral genome is an HIV genome.

13. The replication-defective retrovirus particle as claimed in claim 11, wherein the retroviral genome is an HIV-1 genome.

14. The replication-defective retrovirus particle as claimed in claim 11, wherein the pol gene is modified by deletion of nucleotide sequences thereof.

15. The replication-defective retrovirus particle as claimed in claim 11, wherein the retroviral genome is a pol⁻ construct derived from plasmid pHXB2 with nucleotides 2621–4552 thereof deleted.

16. The replication-defective retrovirus particle as claimed in claim 13, wherein the pseudotyping protein is vesicular stomatitis virus G protein.

17. The replication-defective retrovirus particle as claimed in claim 11, wherein the particle includes a retroviral protein which is an immunological variant of a wild-type retroviral protein.

18. An immunogenic composition to reduce viral load comprising a virus particle as claimed in claim 11 in combination with a pharmaceutically and/or veterinarily suitable excipient.

19. The immunogenic composition as claimed in claim 18, wherein the excipient is selected from the group consisting of a buffer system, a mono-, di-, oligo- or polysaccharide, a viscosity enhancing or tackifying agent, a polymer, a copolymer, a block polymer and a cross-linked polymer.

20. The immunogenic composition as claimed in claim 18, wherein the vaccine is lyophilized.

21. The immunogenic composition as claimed in claim 18, wherein the vaccine is prepared in a form selected from the group consisting of an oral liquid, an oral capsule, a liquid for parenteral injection, a transdermal or transmucosal device and a suppository, and the excipient is a suitable excipient for preparation of the selected form.

22. The immunogenic composition as claimed in claim 18, wherein the retroviral genome is an HIV-1 genome and the pseudotyping protein is VSV-G.

23. The immunogenic composition as claimed in claim 18, further comprising a second replication-defective pol⁻ virus particle representing an immunological variant of the virus particle.

* * * * *